(12) United States Patent
Ante et al.

(10) Patent No.: US 10,393,717 B2
(45) Date of Patent: Aug. 27, 2019

(54) METHOD FOR OPERATING AN OXYGEN SENSOR, COMPUTER PROGRAM PRODUCT AND OXYGEN SENSOR

(71) Applicant: CONTINENTAL AUTOMOTIVE GMBH, Hannover (DE)

(72) Inventors: Johannes Ante, Regensburg (DE); Markus Hien, Bruck i. d. OPF. (DE); Denny Schädlich, Neustadt (DE)

(73) Assignee: Continental Automotive GmbH, Hannover (DE)

( * ) Notice: Subject to any disclaimer, the term of this patent is extended or adjusted under 35 U.S.C. 154(b) by 76 days.

(21) Appl. No.: 15/619,655

(22) Filed: Jun. 12, 2017

(65) Prior Publication Data

US 2017/0356894 A1    Dec. 14, 2017

(51) Int. Cl.
| | |
|---|---|
| *G01N 33/00* | (2006.01) |
| *F02D 41/24* | (2006.01) |
| *G01N 27/416* | (2006.01) |
| *F02D 41/14* | (2006.01) |

(52) U.S. Cl.
CPC ....... *G01N 33/007* (2013.01); *F02D 41/1474* (2013.01); *F02D 41/1495* (2013.01); *F02D 41/2441* (2013.01); *F02D 41/2474* (2013.01); *G01N 27/4163* (2013.01); *G01N 33/0036* (2013.01); *F02D 41/1454* (2013.01); *F02D 2200/70* (2013.01)

(58) Field of Classification Search
USPC .......................................................... 702/89
See application file for complete search history.

(56) References Cited

U.S. PATENT DOCUMENTS

| | | | |
|---|---|---|---|
| 3,984,976 A | 10/1976 | Nagai | |
| 5,375,415 A * | 12/1994 | Hamburg | F02D 41/1476 123/681 |
| 5,473,889 A * | 12/1995 | Ehar | F02D 41/1441 60/276 |
| 6,309,534 B1 * | 10/2001 | Fray | G01N 27/407 204/427 |
| 2006/0213771 A1 * | 9/2006 | Routbort | G01N 27/4073 204/424 |
| 2015/0101327 A1 * | 4/2015 | Clark | F02D 41/0052 60/599 |
| 2016/0061151 A1 * | 3/2016 | Ismail | F02D 41/0052 123/568.21 |
| 2016/0103095 A1 * | 4/2016 | Surnilla | G01N 27/41 205/784.5 |
| 2016/0245193 A1 * | 8/2016 | Makled | F02D 19/088 |
| 2017/0205314 A1 * | 7/2017 | McQuillen | G01M 15/104 |

FOREIGN PATENT DOCUMENTS

| | | |
|---|---|---|
| DE | 10330742 A1 | 1/2005 |
| DE | 102012200062 B4 | 7/2015 |

* cited by examiner

Primary Examiner — Paul D Lee

(57) ABSTRACT

A method and apparatus for compensates for oxygen sensor aging determines a correction of by measuring oxygen content above a specified threshold value and measuring current flowing through the sensor over time.

7 Claims, 1 Drawing Sheet

METHOD FOR OPERATING AN OXYGEN SENSOR, COMPUTER PROGRAM PRODUCT AND OXYGEN SENSOR

FIELD OF THE INVENTION

The invention relates to a method for operating an oxygen sensor having a sensor element for the intake tract of an internal combustion engine. It also relates to a computer program product and an oxygen sensor having a sensor element for the intake tract of an internal combustion engine.

An example of an internal combustion engine having an oxygen sensor arranged in the air intake tract is disclosed in DE 10 2012 200 062 A1. Oxygen sensors are arranged in the intake tract of internal combustion engines to enable regulation of exhaust gas recirculation. In particular, sensors having a sensor element composed of yttrium-stabilized zirconium dioxide ceramic are employed in this case as oxygen sensors. Such a sensor is typically manufactured with platinum electrodes and is very stable against aging. However, due to the high temperatures of approx. 780° C. required for proper operation, a certain amount of aging does occur.

It is known to compensate for an age-related loss of sensitivity of linear lambda probes fitted in the exhaust tract either partially or wholly by employing a special control module that measures the impedance of the reference cell. If the impedance of the reference cell increases due to aging, the heating power is increased until the desired impedance is reached again. Due to the increase in temperature, the sensitivity increases, and the aging is therefore compensated for.

However, the present invention is based on a type of sensor that has no reference chamber and no reference electrode, and so the cell impedance of the reference cell cannot be employed for aging correction. Instead, the cell impedance of the measurement cell is dependent on the oxygen content to be measured, and it therefore cannot be directly employed for aging correction.

The object of the present invention is therefore that of specifying a method for operating an oxygen sensor having a sensor element for the intake tract of an internal combustion engine that can be used to avoid an adverse influence on the exhaust gas recirculation rate due to aging of the sensor element. In addition, a computer program product for executing such a method and an oxygen sensor having a sensor element for the intake tract of an internal combustion engine are to be specified.

This object is achieved by means of the subject matter of the independent patent claims.

Advantageous configurations and extensions of the invention form the subject matter of the dependent claims.

According to one aspect of the invention, a method is specified for operating an oxygen sensor having a sensor element for the intake tract of an internal combustion engine, wherein aging of the sensor element is compensated for as a function of an operating time of the sensor element, wherein the aging compensation comprises an overcompensation of the aging and a correction of the aging compensation in cases where the oxygen sensor measures an oxygen content above a specified threshold value.

This method has the advantage that aging of the sensor element is compensated for while the aging compensation is simultaneously verified.

The method assumes that, while the effect of aging of the sensor element can be approximately estimated, it cannot be done with sufficient accuracy to be able to rely permanently on the aging compensation performed on the basis of this method.

It is therefore suggested that a slight overcompensation of aging be performed. During the operating time of the sensor element, this systematically causes slightly higher measured values of the oxygen content. However, these are problematic because the system does not permit the oxygen content in the intake tract to rise higher than the oxygen content of the ambient air, approximately 21% by volume. The oxygen content of the ambient air can therefore be specified as a threshold value, which may not be exceeded. If measured values occur that are above this specified threshold value, the presumption is that they are the result of overcompensation of the aging. If such excessive oxygen content values above the specified threshold value are measured, the aging compensation is, as a consequence, corrected. This correction can, for example, be effected by comparing the highest measurements of oxygen content against the oxygen content of the ambient air, thereby determining a correction factor for the aging compensation.

The method comprises ascertaining an operating time of the sensor element. One approach to achieving this, for example, is to install an operating hours counter in the electronics of the oxygen sensor. The aging compensation is performed in accordance with the state of the operating hours counter. For example, the aging compensation can be performed at fixed operating time intervals, for example every 100 hours.

According to one embodiment of the invention, the magnitude of the aging compensation is dependent on the operating time of the sensor element. This means that at the beginning of the service life of the sensor element the correction of the sensor readings performed due to aging compensation is higher in amount than later on, when the sensor has already been in operation for a certain period of time. In said embodiment, the typically more rapid aging of the sensor at the beginning of its service life compared to later is taken into account.

In accordance with a further embodiment, the aging compensation is performed depending on a contamination level of the sensor element. As has been ascertained, increased build-up of oil ash, for example, severely contaminates the sensor element, causing it to age faster. According to this embodiment, such contamination of the sensor element leading to more rapid aging is, along with the operating time of the sensor element, taken into account when determining the aging compensation.

However, it is also possible that the aging compensation is performed at fixed operating time intervals, and the magnitude thereof is independent of the operating time of the sensor element.

According to this embodiment, the aging compensation is performed at regular intervals, but always at the same magnitude. Less rapid aging associated with increasing age of the sensor element is not taken into consideration in this case. Though less accurate, at least towards the end of the service life of the sensor, this embodiment has the advantage of being particularly simple. The operating time of the sensor element only plays the role of a "timer clock" for performing the aging compensation, which is always performed at the same magnitude.

According to a further embodiment, the oxygen content of the ambient air is used as a threshold value. This has the advantage that a reliable, fixed value is used as a threshold value. Since the intake air has an oxygen content no higher than the ambient air and recirculated exhaust gas has a lower oxygen content, any measurement of the sensor element having a higher oxygen content than the ambient air can be judged as incorrect. The incorrect measurement, according to this embodiment, is attributed to overcompensation for aging.

According to one embodiment, correction of the aging compensation is performed when the oxygen sensor delivers, over a specified time period, at least a specified number of measured values of oxygen content above the specified threshold value. Such a specified time period can, for example, be at least 5 to 15 minutes.

According to this embodiment, a correction of the aging compensation is only performed when multiple incorrect measurement values occur. With this embodiment, statistical errors of the measurement process are taken into account, to ensure that individual oxygen measurement outliers do not inevitably lead to a correction of the aging compensation.

According to a further aspect of the invention, a computer program product is specified, having a computer-readable medium and program code stored on the computer-readable medium, which, if executed on a processing unit, causes the processing unit to execute the method described.

According to a further aspect of the invention, an oxygen sensor having a sensor element for the intake tract of an internal combustion engine is specified, wherein the sensor element has an ion conductor composed of an yttrium-stabilized zirconium oxide ceramic and wherein the oxygen sensor is assigned a control device, which is configured for operating an oxygen sensor having a sensor element for the intake tract of an internal combustion engine, wherein the control device is configured to compensate for aging of the sensor element as a function of an operating time of the sensor element, wherein the aging compensation comprises an overcompensation of the aging and a correction of the aging compensation in cases where the oxygen sensor measures an oxygen content above a specified threshold value.

In particular, the control device assigned to the oxygen sensor is configured for controlling the described method.

BRIEF DESCRIPTION OF THE FIGURES

Hereinafter, the invention is described in greater detail by means of exemplary embodiments with reference to the appended drawings, in which.

DETAILED DESCRIPTION

Figure 1:
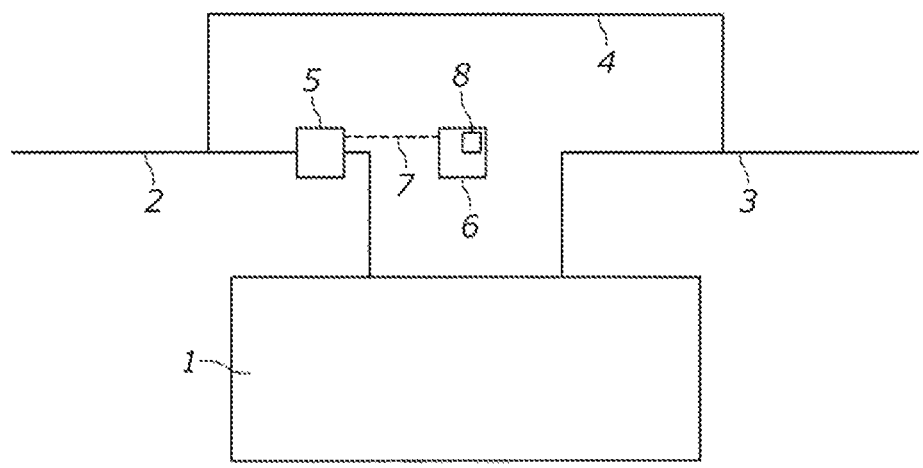
FIG. 1 is a schematic diagram of an internal combustion engine having an intake tract and an oxygen sensor arranged therein according to an embodiment of the invention.

FIG. 1 shows an internal combustion engine 1, which can be implemented, for example, as a gasoline or diesel engine of a vehicle. The internal combustion engine 1 is assigned an intake tract 2, through which combustion air is fed to the internal combustion engine 1. Furthermore, the internal combustion engine 1 is assigned an exhaust tract 3, through which exhaust gases of the internal combustion engine 1 can be discharged.

The internal combustion engine 1 has a system for exhaust gas recirculation, in which exhaust gases from the exhaust tract 3 are recirculated via an exhaust gas recirculation pipe 4 into the intake tract 2. In this way, knocking combustion, in particular, can be avoided in an economical and environmentally friendly fashion. The exhaust gas recirculation rate 4 is regulated using a system that is not shown in the schematic representation according to FIG. 1. To regulate the exhaust gas recirculation rate this system requires, in particular, measurement values from an oxygen sensor 5, arranged in the intake tract between the junction of the exhaust gas recirculation pipe 4 and the internal combustion engine 1.

The oxygen sensor 5 has a sensor element composed of an yttrium-stabilized zirconium oxide ceramic. The sensor 5 is assigned a control device 6, which is connected to the oxygen sensor 5 via a signal cable 7 and which receives the measured values from the oxygen sensor 5 and controls the sensor 5. The control device 6 can be the engine control device of the internal combustion engine 1, however, it can also be a separate sensor control device.

The control device 6 has a computer-readable medium 8, which can be implemented, in particular, as a non-volatile memory and on which program code is stored, which, when executed on the control device 6, instructs the control device 6 to execute the following method:

The control unit 6 records the operating time of the sensor element of the oxygen sensor 5 and compensates for aging of the sensor element by initially performing a computational overcompensation of the aging and subsequently a correction of the aging compensation in cases where the oxygen sensor measures an oxygen content above a specified threshold value. The threshold value employed is the oxygen content of the ambient air of approximately 21% by volume.

In the process, the oxygen content is measured, for example, by measuring the pumping current required to pump oxygen through the zirconium membrane of the sensor. From this, the oxygen content is determined, for example, on the basis of the formula $$O_2 = r*(a + b*I_{pump} + c*I_{pump}^2),$$

wherein $I_{pump}$ is the measured pumping current, a, b and c are factors for quadratic factory calibration, and r is the recalibration factor for aging compensation. During factory calibration r is set to 1 and is later used to compensate for aging-related loss of sensitivity of the sensor.

Due to the initial overcompensation of the aging, the control device 6 initially typically determines slightly too high values of the oxygen content in the intake air. However, if this deviation is too large, oxygen content values above the specified threshold value occur and correction of the aging compensation is triggered.

This results in a periodic self-calibration of the oxygen sensor 5. Although at first, slightly increased oxygen content values are typically determined, the correction of the aging compensation ensures, nevertheless, that this systematic overestimation of the oxygen content does not exceed a specified level.

Figure 2:
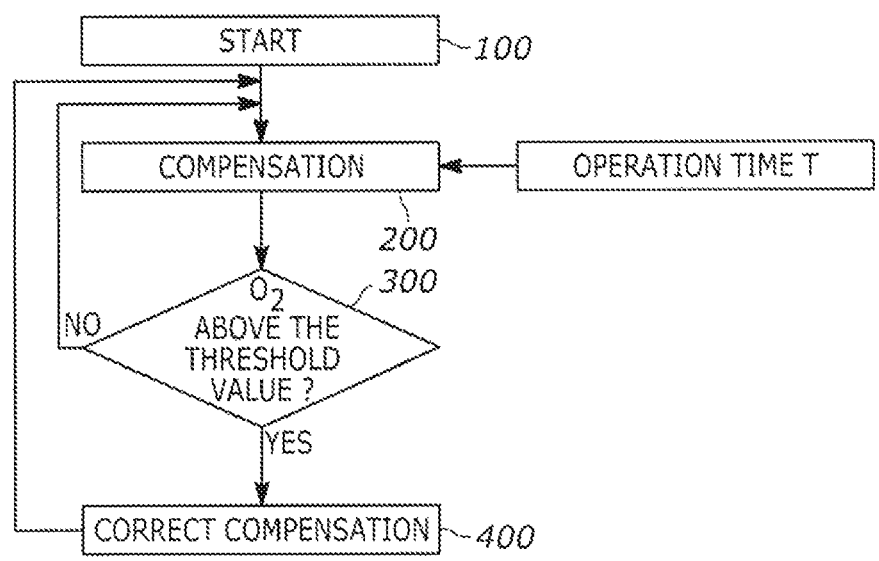
FIG. 2 is a schematic diagram of a flow diagram of a method for operating the oxygen sensor according to FIG. 1.

FIG. 2 illustrates the sequence of a method for operating the oxygen sensor 5 according to FIG. 1. In a step 100 the method is started. For example, the oxygen sensor 5 is put into operation when the internal combustion engine 1 is started.

In a step 200 an aging compensation is performed by mathematically correcting the oxygen concentrations determined by the sensor 5, as a function of the operating time t of the sensor 5 using a compensation factor.

In a step 300 the aging-compensated results thus determined are checked to ascertain whether they represent oxygen content values in the intake tract 2 that are higher than a specified threshold value. If this is not the case, the method is continued.

If oxygen levels above the threshold value are output, then a correction of the aging compensation is made in a step 400, after which the method is continued.

What is claimed is:

1. A method for operating an exhaust gas recirculation system having an oxygen sensor element for an intake tract of an internal combustion engine, wherein oxygen sensor element aging is compensated for as a function of oxygen sensor element operating time, the method comprising;

providing a first amount of exhaust gas from the internal combustion engine into the intake tract and providing ambient air into the intake tract to provide a gaseous mixture of exhaust gas and ambient air to the oxygen sensor element;

measuring a pumping current required to pump oxygen that is in the gaseous mixture of exhaust gas and ambient air, through a zirconium membrane of the oxygen sensor element;

determining oxygen content in the gaseous mixture of exhaust gas and ambient air by evaluating the equation:

$$O_2 = r*(a + b*I_{pump} + c*I_{pump}^2),$$

wherein $I_{pump}$ is the measured pumping current, a, b and c are factors for quadratic factory calibration, and r is a recalibration factor for aging compensation;

changing the value of r, responsive to the operating time of the oxygen sensor element;

and changing the first amount of exhaust gas provided into the intake tract responsive to an oxygen content determined by the oxygen sensor element to be in the gaseous mixture of exhaust gas and ambient air, after the value of r is changed.

2. The method of claim 1, wherein the aging compensation is performed responsive to determining a contamination of the sensor element.

3. The method of claim 1, wherein the aging compensation is performed at fixed operating time intervals, the fixed operating time intervals being determined responsive to the operating time of the sensor element.

4. The method of claim 1, wherein oxygen content of ambient air is used as a threshold value.

5. The method of claim 1, wherein correction of the aging compensation is performed when the oxygen sensor delivers, over a specified time period, at least a specified number of measured values of oxygen content above the specified threshold value.

6. A computer having a computer-readable medium and program code stored in the computer-readable medium, which, when executed causes the computer to execute a method as claimed in claim 1.

7. An apparatus comprising:

an internal combustion engine having an exhaust gas recirculation system comprising an air intake tract, an exhaust tract and an exhaust gas recirculation pipe coupled between the air intake tract and the exhaust tract, the exhaust gas recirculation system being configured to combine engine exhaust gas with ambient air to provide a mixture of exhaust gas and ambient air to the internal combustion engine, the amount of exhaust gas added into the ambient air being determined responsive to a measured level of oxygen in the gaseous mixture;

an oxygen sensor in the gaseous mixture, the oxygen sensor comprising yttrium-stabilized zirconium oxide ceramic;

a computer, operatively coupled to the oxygen sensor;

a memory device operatively coupled to the computer and storing program instructions, which when executed cause the computer to:

compensate for aging of the oxygen sensor as a function of an operating time of the oxygen sensor;

the compensation comprising:

measuring a pumping current required to pump oxygen through a zirconium membrane of the sensor;

determining oxygen content by evaluating the equation:

$$O_2 = r*(a + b*I_{pump} + c*I_{pump}^2),$$

wherein $I_{pump}$ is the measured pumping current, a, b and c are factors for quadratic factory calibration, and r is a recalibration factor for aging compensation;

changing the value of r, responsive to the operating time of the sensor element;

and wherein the apparatus is configured to change the amount of engine exhaust gas provided to the ambient air responsive to an oxygen content that is determined, after the oxygen sensor aging is compensated for.

* * * * *